(12) United States Patent
Shima (10) Patent No.: US 9,113,986 B2
(45) Date of Patent: Aug. 25, 2015

(54) DENTURE AND ARTIFICIAL TOOTH USED IN THE DENTURE

(75) Inventor: Takahiro Shima, Tokushima (JP)

(73) Assignee: SHIKEN CORPORATION, Tokushima (JP)

( * ) Notice: Subject to any disclaimer, the term of this patent is extended or adjusted under 35 U.S.C. 154(b) by 0 days.

(21) Appl. No.: 13/822,950

(22) PCT Filed: Jun. 28, 2011

(86) PCT No.: PCT/JP2011/064766
§ 371 (c)(1),
(2), (4) Date: Mar. 13, 2013

(87) PCT Pub. No.: WO2012/042994
PCT Pub. Date: Apr. 5, 2012

(65) Prior Publication Data
US 2013/0171588 A1 Jul. 4, 2013

(30) Foreign Application Priority Data
Sep. 30, 2010 (JP) ................................. 2010-222958

(51) Int. Cl.
| A61C 13/10 | (2006.01) |
| A61C 13/093 | (2006.01) |
| A61C 13/01 | (2006.01) |
| A61C 13/08 | (2006.01) |

(52) U.S. Cl.
CPC .............. *A61C 13/1006* (2013.01); *A61C 13/01* (2013.01); *A61C 13/04* (2013.01); *A61C 13/08* (2013.01); *A61C 13/10* (2013.01)

(58) Field of Classification Search
CPC .................. A61C 8/005; A61C 8/0048; B29L 2031/7536
USPC ....................... 433/190–193; 264/17; 434/263
See application file for complete search history.

(56) References Cited

U.S. PATENT DOCUMENTS

| 200,284 A | * | 2/1878 | Hall | ............................... 433/192 |
| 638,019 A | | 11/1899 | Justi | |

(Continued)

FOREIGN PATENT DOCUMENTS

| DE | 360002 | 9/1922 |
| FR | 620397 | 4/1927 |

(Continued)

OTHER PUBLICATIONS

International Search Report issued Oct. 4, 2011 in International (PCT) Application No. PCT/JP2011/064766.

*Primary Examiner* — Cris L Rodriguez
*Assistant Examiner* — Mirayda A Aponte
(74) *Attorney, Agent, or Firm* — Wenderoth, Lind & Ponack, L.L.P.

(57) ABSTRACT

The denture has the root of an artificial tooth embedded in a denture base molded from plastic. The artificial tooth is provided with a through-hole in the root that fills with denture base plastic, and the openings at both ends of the through-hole are embedded in the denture base. Further, both ends of the through-hole open at artificial tooth surfaces that face adjacent teeth, and an air-vent is provided that connects with the through-hole. The opening for the air-vent is positioned on a lingual side surface of the artificial tooth that is exposed from the denture base. Plastic that forms the denture base flows into the through-hole and air-vent embedding and retaining the root of the artificial tooth in the denture base.

13 Claims, 6 Drawing Sheets

(56) References Cited

U.S. PATENT DOCUMENTS 1,241,854 A * 10/1917 Justi .............................. 433/192
2,370,488 A * 2/1945 Raber ........................... 433/192
5,632,621 A   5/1997 Moodley

FOREIGN PATENT DOCUMENTS

| | | |
|---|---|---|
| JP | 6-3733 | 4/1931 |
| JP | 2002-238925 | 8/2002 |
| JP | 2008-23104 | 2/2008 |

* cited by examiner

DENTURE AND ARTIFICIAL TOOTH USED IN THE DENTURE

BACKGROUND OF THE INVENTION

1. Field of the Invention

The present invention relates to a denture having the root of an artificial tooth (false tooth) embedded and attached in a plastic denture base (foundation, plate), and to the artificial tooth used in the denture.

2. Description of the Related Art

A denture has the roots of artificial teeth embedded and attached in a denture base made of plastic. The base region of the denture is formed from thermo-setting acrylic resin made up of a mixture including acrylic resin polymer, liquid acrylic resin monomer, and a cross-linking agent. Or, the base region is formed from resins such as thermoplastic polycarbonate resin, polyamide resin, acrylic resin, or polyester resin. Artificial teeth are embedded and attached in the denture base when the base region is formed. Artificial teeth are fabricated from materials such as plastics or ceramics. To embed artificial teeth in the denture base, the roots of the artificial teeth are provisionally held in a plaster mold. In that state, the plaster mold is filled with plastic in a viscous fluid form and thermo-setting plastic is hardened by heating or thermoplastic is hardened by cooling to form the denture. The denture fabricated in this manner has the roots of the artificial teeth embedded and held in the plastic molded denture base.

In a denture of this structure, it is possible for an artificial tooth to separate from (fall out of) the denture base during use. Although an artificial tooth can be made from materials such as plastics, ceramics, or metals, the majority are made of plastic due to its workability, cost, and appearance. Further, the entire artificial tooth or at least the root that embeds in the denture base is commonly fabricated from acrylic resin materials. However, since plastics, including variety of thermoplastics, used to form the denture base region fill the mold in a heated fluid (molten) state and harden by cooling, strong chemical bonding between the artificial tooth and denture base cannot be expected. Particularly such drawback is prominent in case a type of resin material used for the denture base is different from the one of artificial teeth. To resolve this detrimental situation, an artificial tooth has been developed with a through-hole established in the root, and that through-hole is embedded in the denture base region (refer to Japanese Laid-Open Patent Publication 2002-238925).

Figure 1:
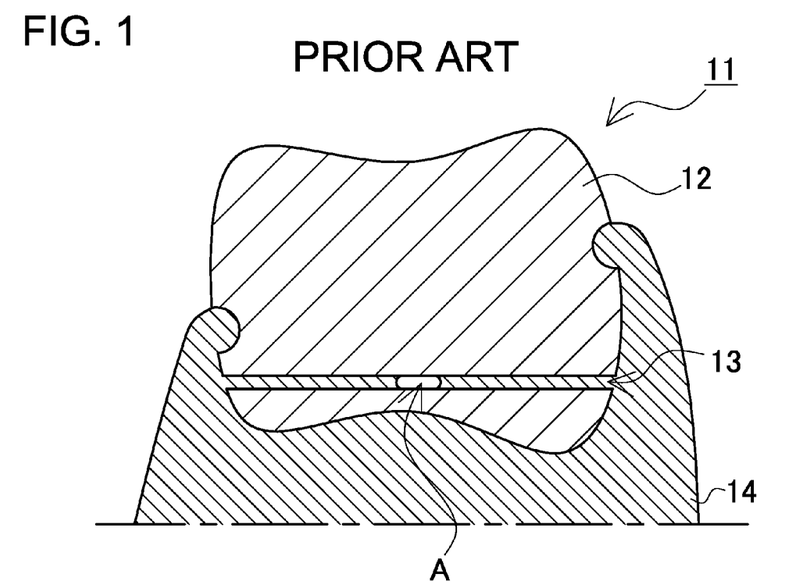
FIG. 1 is a cross-section view showing a prior art denture.

The denture cited in JP 2002-238925 A is shown in FIG. 1. The denture 11 in this figure has denture base 14 plastic that flows into, and hardens inside the through-hole 13 established in the artificial tooth 12. The plastic that flows into, and hardens inside the through-hole 13 connects with the plastic of the denture base 14 and prevents separation of the artificial tooth 12 from the denture base 14. However, during actual processing to fabricate a denture 11 with this configuration, it is extremely difficult to smoothly flow denture base 14 plastic into the artificial tooth 12 through-hole 13. This is because plastic flows into the through-hole 13 from openings at both ends and air A (FIG. 1 label A) trapped inside cannot escape. As long as air inside the through-hole 13 cannot be discharged, the through-hole 13 cannot be completely filled with plastic. This is because the trapped air blocks the flow of plastic into the through-hole 13. Even if the denture mold if filled with plastic in a pressurized manner, the entire through-hole 13 cannot be filled with plastic if air is trapped inside. This is because the trapped air is compressed but still blocks the flow of plastic. A artificial tooth 12 with a through-hole 13 that is not filled with plastic is not strongly connected to the denture base 14. This is because plastic introduced into the through-hole 13 is cut-off and not continuous through the inside the through-hole 13. When an artificial tooth 12 is embedded in the denture base 14 under these conditions, plastic partially filling the through-hole 13 is easily distorted and the artificial tooth 12 can separate from the denture base 14 when the plastic distorts. Consequently, this configuration has the drawback that even though the artificial tooth 12 is provided with a through-hole 13, it cannot be robustly embedded in the denture base 14 in a manner that keeps the tooth from falling out.

Figure 2:
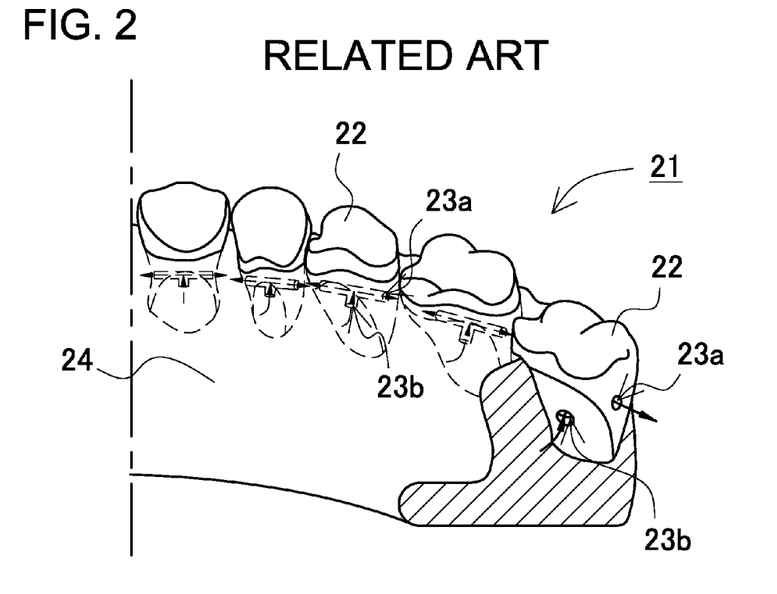
FIG. 2 is a perspective view partially in cross-section of a denture previously developed by the present applicant.

To eliminate this drawback, the present applicant developed the denture shown in FIG. 2. In this denture 21 as well, the root of an artificial tooth 22 is embedded in a molded plastic denture base 24. This artificial tooth 22 is also provided with a through-hole 23a that fills with denture base 24 plastic, and the openings at both ends of the through-hole 23a become buried inside the denture base 24. In addition to establishing the through-hole 23a openings on the surfaces of the artificial tooth 22 that face adjacent teeth on both sides, a vertical hole 23b is established that connects with the through-hole 23a inside the artificial tooth 22. One end of the vertical hole 23b connects with the through-hole 23a, and the other end opens at the bottom-side of the artificial tooth 22. Further, the vertical hole 23b opening is positioned at the bottom-side of the artificial tooth 22 further towards the tip of the root than the through-hole 23a openings. The vertical hole 23b and through-hole 23a fill with the plastic that forms the denture base 24 and robustly hold the root of the artificial tooth 22 embedded in the denture base 24.

The denture 21 described above has an artificial tooth 22 provided with a through-hole 23a having openings in surfaces that face adjacent teeth on both sides, and a vertical hole 23b that connects with the through-hole 23a. One end of the vertical hole 23b connects with the through-hole 23a, the other end opens at the bottom-side of the artificial tooth 22, the vertical hole 23b opening is positioned at the bottom-side further towards the tip of the artificial tooth 22 root than the through-hole 23a openings, and denture base 24 plastic flows into the vertical hole 23b and the through-hole 23a. In particular, the vertical hole 23b of this denture 21 connects with the through-hole 23a and opens below the through-hole 23a further towards the tip of the artificial tooth 22 root than the through-hole 23a. The vertical hole 23b, which has its opening near the bottom of the artificial tooth 22 root, is designed to fill with the viscous fluid plastic of the denture base 24 before the through-hole 23a. In this design, when the vertical hole 23b fills with plastic, plastic does not flow into the through-hole 23a from the through-hole 23a openings. Under these conditions, air is discharged from the through-hole 23a openings by the inflow of plastic from the vertical hole 23b, and the through-hole 23a fills with plastic from the vertical hole 23b. If plastic filling can follow this scenario, air in the vertical hole 23b and through-hole 23a can be smoothly discharged and replaced by denture base 24 plastic. If denture base 24 plastic can fill the vertical hole 23b and through-hole 23a without void formation, the artificial tooth 22 can be solidly connected to the denture base 24 via the plastic and the artificial tooth 22 can be reliably prevented from falling out during use.

See also Japanese Laid-Open Patent Publication 2008-23104

In the denture 21 shown in FIG. 2, the vertical hole 23b and through-hole 23a completely fill with the plastic that forms the denture base 24, and that allows the artificial tooth 22 to be attached in the denture base 24 in a manner that will not fall out. However, to achieve this, plastic must fill the vertical hole before filling the through-hole, and it is necessary for plastic to flow in a manner that discharges vertical hole and through-hole air when it is introduced into the vertical hole. During the fabrication step that forms the denture base, the mold is filled with plastic in viscous fluid form while holding provisionally retained artificial teeth, and precise control of the flow of plastic is difficult. In particular, when plastic is introduced into a plaster mold holding many provisionally retained artificial teeth, it is extremely difficult to introduce plastic initially into the vertical hole of every tooth. If plastic flows in from both the through-hole and the vertical hole of any artificial tooth when the mold is filled with viscous fluid plastic, air residing in the vertical hole or through-hole will not be smoothly discharged. This makes it difficult to attach artificial teeth in the denture base in a manner that will not separate.

The present invention was developed to further resolve the drawbacks described above. Thus, it is an object of the present invention to provide a denture and artificial tooth used in the denture that can solidly attach the artificial tooth in the denture base in a manner that will not fall out without having to precisely control the flow of plastic that forms the denture base.

SUMMARY OF THE INVENTION

To achieve the object described above, the denture and artificial tooth used in the denture of the present invention are configured as follows. The denture for the first aspect of the present invention is provided with a denture base molded from plastic, and an artificial tooth that has its root embedded in the denture base. The artificial tooth is provided with a through-hole in the root that fills with denture base plastic, and the openings at both ends of the through-hole are embedded in the denture base. Further, both ends of the through-hole established in the artificial tooth of this denture open at artificial tooth surfaces that face adjacent teeth, and an air-vent is provided that connects with the through-hole inside the artificial tooth. The opening for the air-vent is positioned on a lingual side surface of the artificial tooth that is exposed from the denture base. Plastic that forms the denture base flows into the through-hole and air-vent to solidly attach the artificial tooth with its root embedded in the denture base.

The artificial tooth used in the denture of the present invention has its root embedded and attached in a denture base made of plastic. The artificial tooth is provided with a through-hole in the root that fills with the plastic that forms the denture base. Denture base plastic flows into the through-hole and the artificial tooth is embedded and attached in the denture base. Further, both ends of the through-hole established in the root of the artificial tooth open at surfaces that face adjacent teeth, and an air-vent is provided that connects with the through-hole inside the artificial tooth. The opening for the air-vent is positioned on a lingual side surface of the artificial tooth that is exposed from the denture base. The artificial tooth is configured to have plastic, which forms the denture base, flow into the through-hole and air-vent, to embed the root in the denture base, and to attach the artificial tooth to the denture base.

The above and further objects of the present invention as well as the features thereof will become more apparent from the following detailed description to be made in conjunction with the accompanying drawings.

DESCRIPTION OF EMBODIMENT(S)

In the denture for an embodiment of the present invention, the air-vent is established in an orientation perpendicular to the through-hole.

In the denture for another embodiment of the present invention, the through-hole and air-vent have circular cylindrical shapes with equal inside diameters.

In the artificial tooth used in the denture for further embodiment of the present invention, the air-vent can be established in an orientation perpendicular to the through-hole.

In the artificial tooth used in the denture for still further embodiment of the present invention, the through-hole and air-vent can have circular cylindrical shapes with equal inside diameters.

One embodiment has the characteristic that the artificial tooth can be solidly attached in the denture base in a manner that will not fall out. This is because in addition to a through-hole with both ends open at surfaces facing adjacent teeth, the artificial tooth is provided with an air-vent that connects with the through-hole. Further, the air-vent opening is positioned on a lingual side surface of the artificial tooth that is exposed from the denture base, and denture base plastic flows into the through-hole and air-vent. The air-vent, which is opened on a lingual side surface of the artificial tooth exposed from the denture base, fills with denture base plastic in viscous fluid form from the through-hole. When plastic flows into the through-hole, there is no plastic filling the air-vent and through-hole air is smoothly discharged. Since the air-vent is opened on a lingual side surface of the artificial tooth exposed from the denture base, the air-vent opening is closed off from chamber of the plaster mold during the fabrication step to mold the plastic denture base. Although the plaster mold is impermeable to plastic, it allows air to pass through. Therefore, air displaced by injection of plastic into the through-hole is smoothly discharged from the air-vent through the plaster mold to the outside. Further, since the air-vent opening, which is positioned in a region exposed from the denture base, is closed off by the plaster mold, plastic to form the denture base is not injected into that opening. Consequently, during the process step that injects plastic into the through-hole, air in the through-hole is reliably discharged out the air-vent. Plastic filling the through-hole flows from the through-hole into the air-vent, and the air-vent fills with plastic. Plastic is introduced into the air-vent only from the side connected to the through-hole. For this reason, during the process step that fills the air-vent with plastic, air can be reliably discharged from the air-vent opening, which is closed off from the chamber of the plaster mold. Therefore, the air-vent as well has no residual trapped air and can be filled with plastic without void formation. Although the opening of the plastic-filled air-vent is on an exposed surface of the artificial tooth, that surface is on the side of the artificial tooth that faces the tongue (inside of the mouth) and cannot be seen from the outside.

Accordingly, the embodiment has the characteristic that both the through-hole and air-vent can be filled with denture base plastic while smoothly and reliably discharging the air inside via the air-vent, which connects with the artificial tooth through-hole and opens in a designated location. The denture base formed with plastic, which fills the through-hole and air-vent, is solidly connected with the artificial tooth, and can reliably prevent the artificial tooth from falling out during use.

In addition, since through-hole openings are established in artificial tooth surfaces that face adjacent teeth and the air-vent is opened on a lingual side surface of the artificial tooth, the embodiment has the characteristic that the through-hole and air-vent openings do not standout visually and the artificial tooth can be solidly attached to the denture base in a manner that will not fall out while maintaining the same external appearance as prior art artificial teeth.

Figure 3:
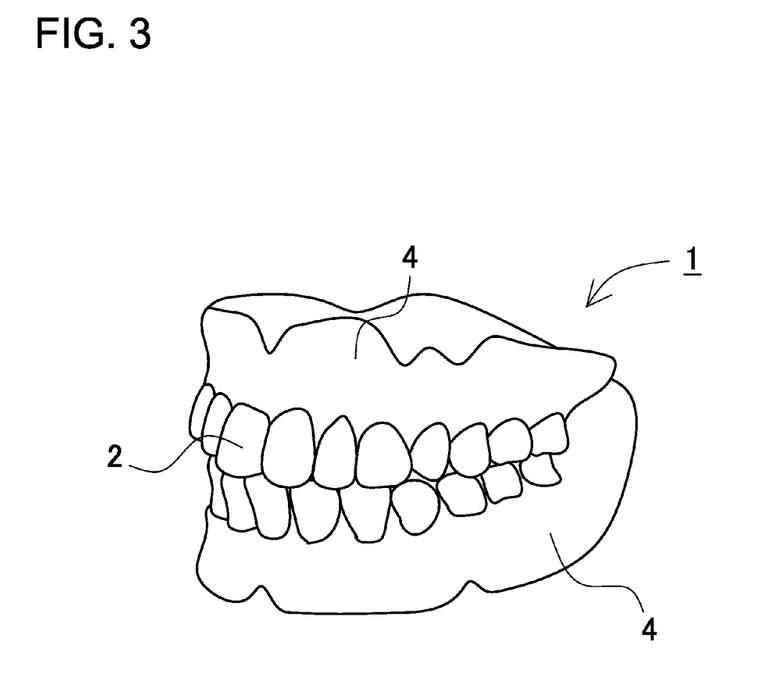
FIG. 3 is a perspective view of dentures for an embodiment of the present invention.

FIG. 3 shows dentures 1 composed of denture bases 2 with a plurality of artificial teeth 2. The dentures 1 in this figure have a complete set of anterior (incisor and canine) and posterior (premolar and molar) artificial teeth 2 attached in denture bases 4. However, the denture of the present invention is not limited to a configuration having a complete set of anterior and posterior artificial teeth attached in a denture base. Specifically, the present invention is not limited to complete dentures or full dentures designed for individuals with no teeth. The denture of the present invention is also applicable to a partial denture used by individuals with some missing teeth. Specifically, the present invention is applicable to configurations that attach some anterior or posterior artificial teeth in a denture base, or that attach only anteriors or only posteriors in a denture base. In the same manner as natural teeth, a plurality of artificial teeth 2 is attached in a denture base 4 adjacent to one another and such that the boundaries of the artificial teeth 2 establish an interior concave region. As shown in FIG. 3, each artificial tooth 2 is attached in a denture base 4 with one section, which is the root, embedded in the denture base 4, and with the remaining tooth surface section protruding out from the denture base 4.

Figure 4:
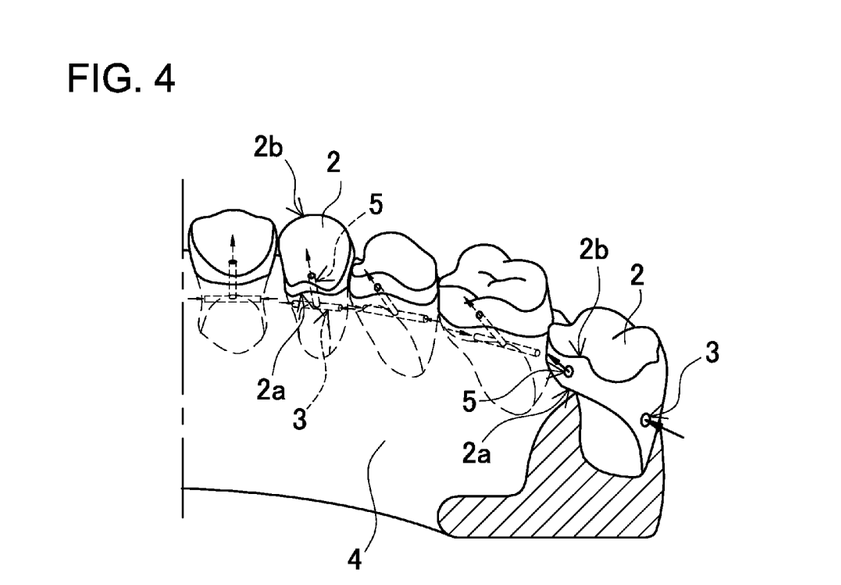
FIG. 4 is a perspective view partially in cross-section of the lower jaw (mandible) denture shown in FIG. 3 as viewed from the side that faces the inside of the mouth.
Figure 5:
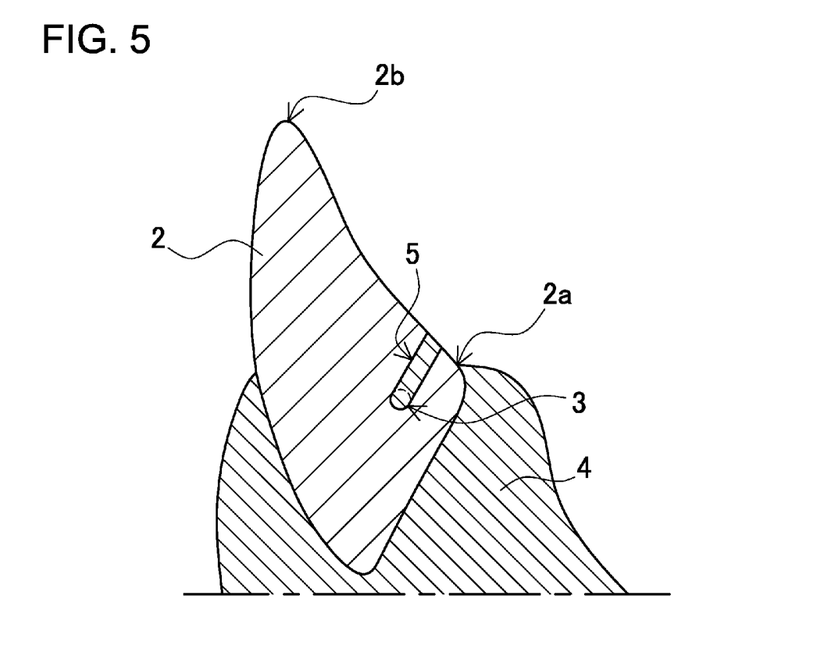
FIG. 5 is a vertical cross-section through the denture shown in FIG. 4.

FIG. 4 is an oblique view partially in cross-section of the lower jaw denture 1 shown in FIG. 3 as viewed from the side that faces the inside of the mouth. FIG. 5 is a vertical cross-section through the denture 1 shown in FIG. 4. In FIGS. 4 and 5, each artificial tooth 2 has a through-hole 3 established inside with ends that open at surfaces facing adjacent teeth on both sides. The through-hole 3 fills with plastic that forms the denture base 4, the plastic forms a continuous unit with the denture base 4, and the artificial tooth 2 is solidly connected with the denture base 4. The through-hole 3 is established as circular cylindrical hole with a 1 mm inside diameter that traverses laterally across the inside of the artificial tooth 2. The through-hole 3 is formed with a drill. The through-hole 3 can also be made smaller or larger than 1 mm. However, if it is too small, it becomes difficult to fill with plastic, the strength of the connection between the plastic filling the through-hole 3 and the plastic of the denture base 4 decreases, and connection between the artificial tooth 2 and the denture base 4 weakens. Consequently, the diameter of the through-hole 3 is made at least greater than or equal to 0.5 mm. Conversely, if the through-hole 3 is too large, the strength of the part of the artificial tooth 2 that is embedded in the denture base 4 decreases. Accordingly, the diameter of the through-hole 3 is preferably less than 3 mm, and more preferably less than 2 mm.

Each artificial tooth 2 is also provided with an air-vent 5 that connects with the through-hole 3 inside the tooth. One end of the air-vent 5 connects with the through-hole 3 and the other end opens at the surface of the artificial tooth 2. Further, the air-vent 5 opens in a region of the artificial tooth 2 exposed from the denture base 4 on a lingual side surface between the upper ridge of the root 2a at the bottom-side of the tooth and the cutting edge (incisor edge) 2b at the upper-side of the tooth. This allows air in the through-hole 3 and air-vent 5 to be smoothly discharged when the plaster mold is filled with plastic to form the denture base 4. The air-vent 5 is a circular cylindrical hole with an inside diameter of approximately 1 mm. After the through-hole 3 is drilled open, the air-vent is formed by drilling. The same as for the through-hole 3, the air-vent can also be made smaller or larger than 1 mm, but if it is made too small, it cannot be smoothly filled with plastic. Accordingly, the diameter of the air-vent 5 is also made at least greater than or equal to 0.5 mm. Further, since the strength of the part of the artificial tooth 2 that is embedded in the denture base 4 decreases if the air-vent 5 is too large, the diameter of the air-vent 5 is preferably less than 3 mm, and more preferably less than 2 mm. The inside diameter of the air-vent 5 is made equal to that of the through-hole 3, or it is made larger than the through-hole 3.

In the artificial teeth 2 in FIGS. 4 and 5, the air-vent 5 connects to the center region of the through-hole 3. Further, the air-vent 5 is established approximately perpendicular to the through-hole 3. This artificial tooth 2 configuration allows plastic filling the through-hole 3 from both ends to flow into the air-vent 5 at the center and reliably discharge through-hole 3 air from the air-vent 5, and allows plastic to smoothly and completely fill the through-hole 3 and air-vent 5.

Although the through-hole 3 and air-vent 5 of the artificial tooth 2 described above connect in an approximately perpendicular manner, the angle of intersection of the two holes is not limited to that arrangement. For example, it is also possible to connect the air-vent 5 to the through-hole 3 at an obliquely inclined angle and extend the length of the air-vent 5. This structure allows the plastic that forms the denture base 4 to smoothly fill the through-hole 3 and air-vent 5 and, as described later, has the effect of increasing adhesion between the artificial tooth 2 and plastic filling the holes.

Further, although the through-hole 3 in the artificial tooth 2 described above is opened in a straight line in the direction of the row of teeth (in the mesiodistal direction in dental terms), the through-hole does not necessarily have to be opened in a straight line. For example, the through-hole can incline upward from the openings at both ends towards the air-vent in the center region to form an inverted v-shape (hill-shape). Or, the through-hole can decline downward from the openings at both ends towards the center air-vent to form a v-shape (valley-shape). In these artificial tooth configurations as well, plastic introduced from both ends of the through-hole flows into the center air-vent, and the through-hole and air-vent can be smoothly and completely filled with plastic.

Figure 6:
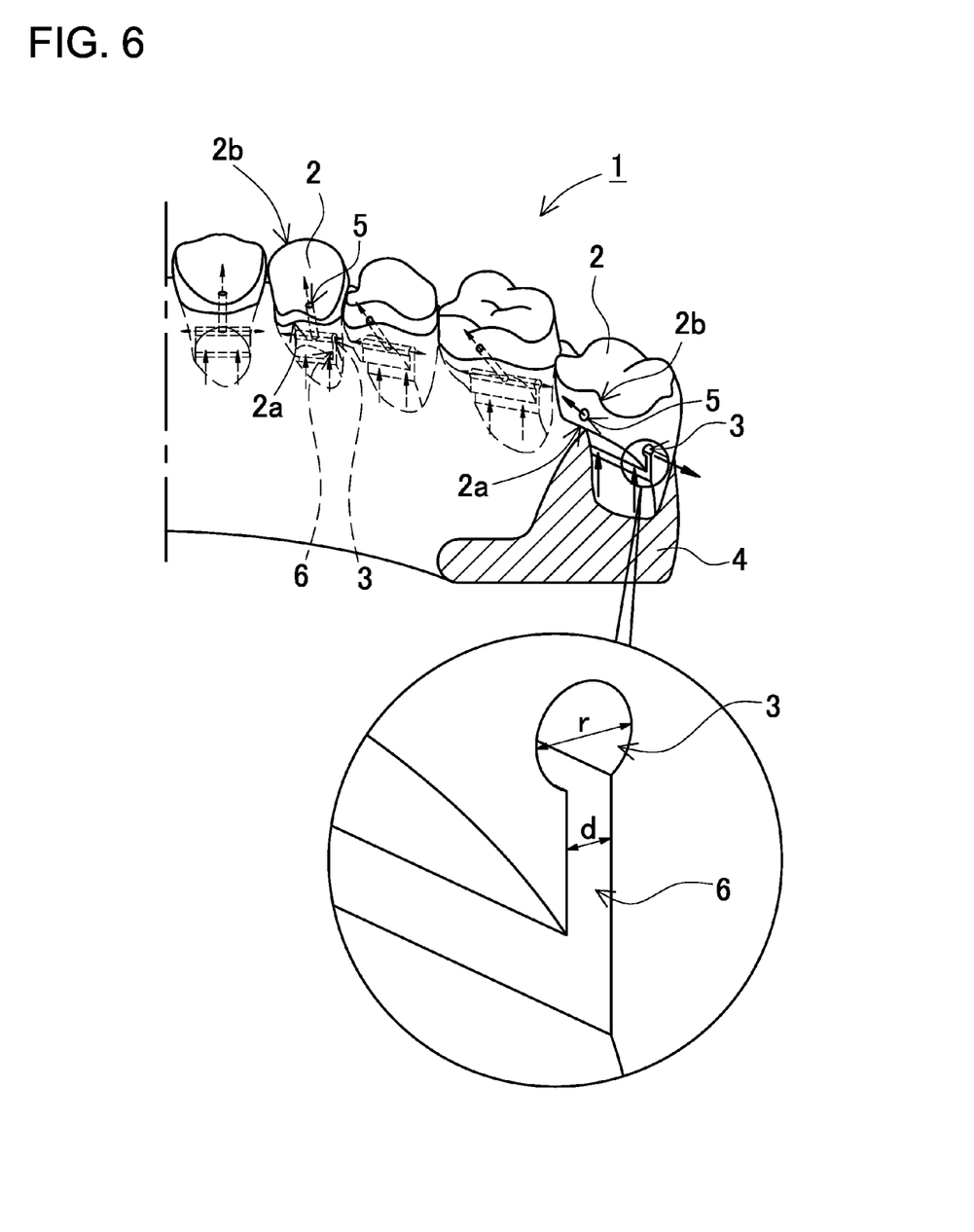
FIG. 6 is a perspective view partially in cross-section of a lower jaw denture for another embodiment of the present invention as viewed from the side that faces the inside of the mouth.
Figure 7:
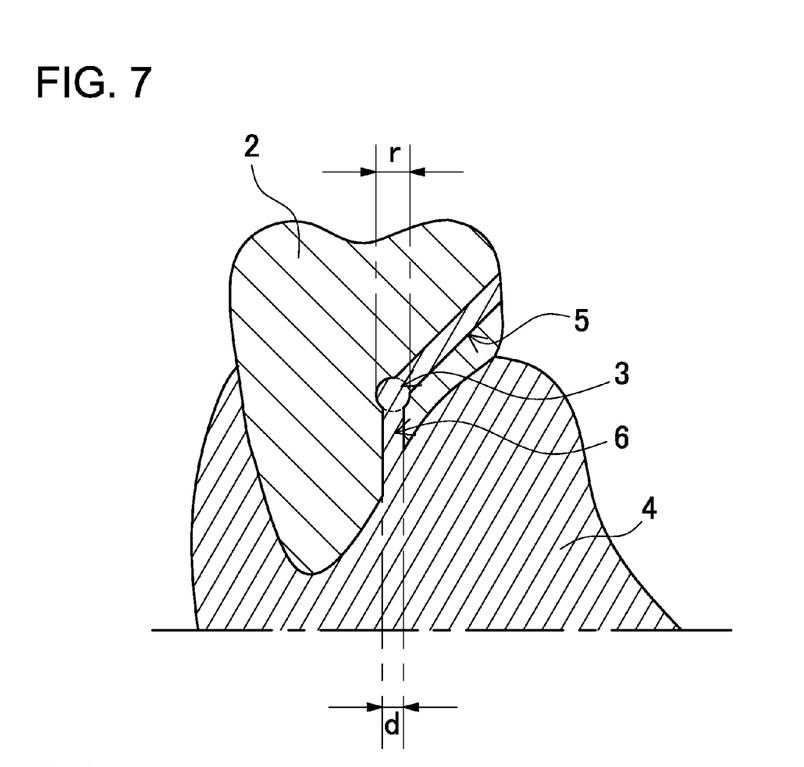
FIG. 7 is a vertical cross-section through the denture shown in FIG. 6.

Turning to the artificial teeth 2 shown in FIGS. 6 and 7, a through-hole 3 is provided inside each artificial tooth 2 with openings at both ends that face adjacent teeth, an air-vent 5 is provided that connects with the through-hole 3, and a slit 6 is provided at the bottom-side or root-side of the through-hole 3. One side of the slit 6 connects with the through-hole 3 and the other side opens at the root of the artificial tooth 2. Each artificial tooth 2 shown in the figures has a slit 6 extending along the length of the through-hole 3, and both ends of the slit 6 open on surfaces facing adjacent teeth. Specifically, each artificial tooth 2 shown in the figures has a slit 6 established along the entire length of the through-hole 3 to form an overall channel shape. However, the slit does not necessarily have to be established along the entire length of the through-hole and can be established only in the end regions of the through-hole or only at one end of the through-hole as well.

The slit 6 shown in the figures is formed with an interior width (d) that is smaller than the inside diameter (r) of the through-hole 3. A artificial tooth 2 with a slit 6 made narrower than the through-hole 3 diameter can be more solidly attached in a manner that will not fall out when those regions are filled with plastic. This is because the narrow slit 6 size prevents hardened plastic filling the wider through-hole 3 from pulling out through the slit 6, and reliably prevents the artificial tooth 2 from falling out. To implement this structure, the through-hole 3 diameter (r) to slit 6 width (d) ratio is made, for example, 1.1 to 2.0, and preferably is made 1.1 to 1.5. However, in a structure with a slit established only at the end regions of the through-hole or only at one end region with no slit-through-hole connection in the center region, the interior width of the slit can be made greater than or equal to the inside diameter of the through-hole and the still prevent the artificial tooth from falling out.

The through-hole 3 and air-vent 5 are formed in the artificial tooth 2 with a drill and the slit 6 is cut out with a rotating disk-shaped cutting tool. The interior width of the slit 6 is made less than or equal to 1 mm, or it can also be made greater than or equal to 1 mm. However, if the slit 6 width is too small, it becomes difficult to fill with plastic, the strength of the connection between the plastic filling the slit 6 and the plastic of the denture base 4 decreases, and connection between the artificial tooth 2 and the denture base 4 weakens. With a slit 6 width greater than or equal to 0.5 mm, the artificial tooth 2 can be attached to the denture base 4 in a manner that will not fall out. However, if the slit 6 width is too large, the strength of the part of the artificial tooth 2 that is embedded in the denture base 4 decreases. Accordingly, the interior width (d) of the slit 6 is preferably less than 3 mm, and more preferably less than 2 mm. In an artificial tooth 2 provided with a slit 6 connected to the through-hole 3, air is discharged from the air-vent 5 when denture base 4 plastic is introduced into the slit 6 and through-hole 3, and that allows plastic to flow smoothly into the slit 6 and through-hole 3.

Figure 8:
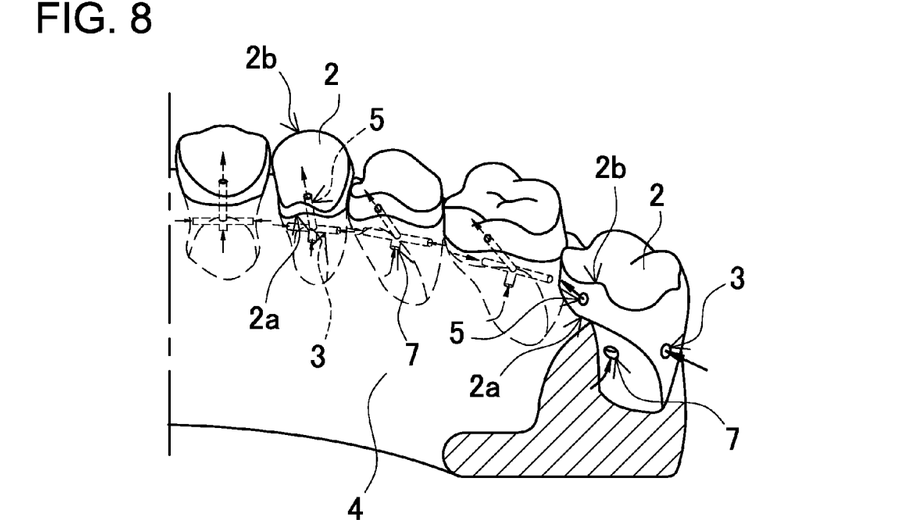
FIG. 8 is a perspective view partially in cross-section of a lower jaw denture for another embodiment of the present invention as viewed from the side that faces the inside of the mouth.
Figure 9:
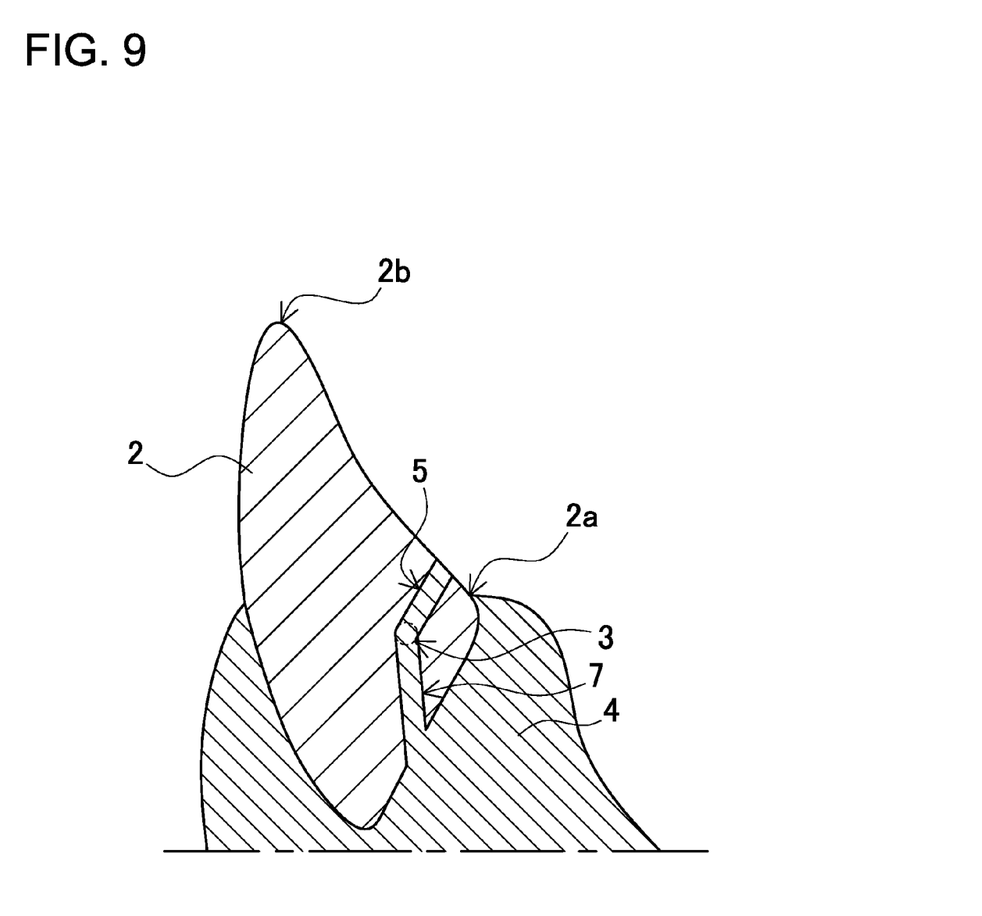
FIG. 9 is a vertical cross-section through the denture shown in FIG. 8.

Next, turning to the artificial teeth 2 shown in FIGS. 8 and 9, a through-hole 3 is provided inside each artificial tooth 2 with openings at both ends that face adjacent teeth, an air-vent 5 is provided that connects with the through-hole 3, and a vertical hole 7 is provided that connects with the through-hole 3 inside the artificial tooth 2. One end of the vertical hole 7 connects with the through-hole 3, and the other end opens on the root-side of the artificial tooth 2. In addition, the opening of the vertical hole 7 is established further towards the tip of the root than the through-hole 3 openings to allow denture base 4 plastic to smoothly fill the vertical hole 7. The vertical hole 7 is established as a circular cylindrical hole with a 1 mm inside diameter. The vertical hole 7 is formed with a drill after the through-hole 3 has been drilled open. The same as for the through-hole 3, the vertical hole 7 can be made smaller or larger than 1 mm. However, if it is too small, it becomes difficult to fill with plastic, the strength of the connection between the plastic filling the vertical hole 7 and the plastic of the denture base 4 decreases, and connection between the artificial tooth 2 and the denture base 4 weakens. Consequently, the diameter of the vertical hole 7 is made at least greater than or equal to 0.5 mm. Conversely, if the vertical hole 7 is too large, the strength of the part of the artificial tooth 2 that is embedded in the denture base 4 decreases. Accordingly, the diameter of the vertical hole 7 is preferably less than 3 mm, and more preferably less than 2 mm. The inside diameter of the vertical hole 7 is made equal to that of the through-hole 3, or it is made larger than the through-hole 3. In an artificial tooth 2 provided with a vertical hole 7 connected to the through-hole 3, air is discharged from the air-vent 5 when denture base 4 plastic is introduced into the vertical hole 7 and through-hole 3, and that allows plastic to flow smoothly into the vertical hole 7 and through-hole 3. Although the vertical holes 7 in FIG. 8 are shown as circular holes, the vertical holes 7 can also have a slit shape.

(Materials)

The artificial teeth 2 described above are fabricated to have the same form as natural teeth from synthetic resin, ceramics, or metal. The surface of an artificial tooth 2 formed from synthetic resin or ceramics is colored to match a natural tooth, or appropriate coloring is added to the synthetic resin or ceramics used to form the artificial tooth 2. Acrylic resin or synthetic resins such as polycarbonate resin are used to form an artificial tooth 2. The artificial tooth 2 can also be formed by casting metal. For example, a metal artificial tooth 2 can be made from alloys such as gold alloy or gold-silver-palladium alloy.

The denture base 4 is made to have the same external appearance as natural tooth gum. However, the denture 1 is not necessarily limited to gum attachment. For example, since there are also dentures that connect and attach to adjacent remaining teeth, the denture base 4 is fabricated in a shape that is optimal for the attachment configuration. The denture base 4 can be molded from synthetic resin such as acrylic resin or polycarbonate resin. The synthetic resin that forms the denture base 4 is colored to match natural tooth gum color and has red pigmented fibers included in the resin mix. This type of denture base 4 closely approximates the appearance of natural tooth gum. This is because the red fibers have an appearance similar to blood vessels in the gum. There are also denture bases 4 called metal based that include one part made as a metal plate. However, a metal based denture uses synthetic resin in the jaw ridge region where artificial teeth connect to the base with the purpose of embedding and attaching the artificial teeth also in mind. The form of the denture base is determined based on missing tooth gum and alveolar bone restoration, physiology, function, and appearance.

In the embodiments described above, similar acrylic resin systems are used in both the artificial tooth 2 and denture base 4. This is because acrylic resin is colorless, transparent, hard, and has superior resistance to corrosive degradation over time. In particular, among the well known resins, acrylic resin has the highest degree of transparency, is robust, safe, and is easy to pigment and process. Further, using the same materials for both the artificial tooth 2 and denture base 4 has the benefit of increasing adhesion between the two.

(Fabrication Process Steps)

A denture 1 with artificial teeth 2 embedded in the denture base 4 is fabricated in the following manner.

1. Artificial teeth are arranged in a wax denture base according to an impression taken of the patient's teeth to form a wax denture.

2. The wax denture formed in step 1 is placed in metal container, plaster is poured around the wax denture, and the plaster is hardened. This buries the wax denture formed in step 1 inside a plaster mold.

3. The plaster mold formed in step 2 is heated to melt the wax, and the melted wax is removed from the plaster to form a plaster mold with a hollow chamber in the denture base molding region. Artificial teeth are provisionally set in the plaster mold in a manner that projects the roots into the hollow denture base molding chamber. Parts of the artificial teeth that project into the molding chamber become embedded in the denture base.

4. The hollow chamber of the plaster mold is filled with unhardened synthetic resin such as an acrylic resin in viscous fluid form.

5. The unhardened synthetic resin is polymerized and hardened to create a denture with roots of the artificial teeth embedded in the denture base.

6. The denture is separated from the plaster mold.

The following describes steps 3 and 4 above in more detail. In step 3, wax is melted and removed from the plaster mold to form the hollow mold chamber, and unhardened synthetic resin is introduced into the chamber to form the denture base in step 4. For the artificial teeth in FIGS. 4 and 5, unhardened synthetic resin in viscous fluid form fills the through-hole 3 and air-vent 5 established in each artificial tooth 3 to increase the strength of connection between the denture base 4 and the artificial teeth 2. More specifically, when unhardened synthetic resin in viscous fluid form fills the plaster mold chamber formed (in step 3) by wax removal, resin flows into each artificial tooth 2 through-hole 3 from both ends. Unhardened synthetic resin flowing into the through-hole 3 flows from the through-hole 3 into the air-vent 5. At that time, air residing in the through-hole 3 and air-vent 5 is discharged from the air-vent 5 opening. Since the air-vent 5 opening is positioned in an exposed part of the artificial tooth 2 and not inside the denture base 4, the air-vent 5 opening is closed off by the plaster mold. The plaster mold that closes off the air-vent 5 opening is porous to air but not to unhardened synthetic resin. Accordingly, during the process step that introduces unhardened synthetic resin into the through-hole 3, air escapes from the through-hole 3 and air-vent 5 through the air-vent 5 opening, and unhardened synthetic resin flows from the through-hole 3 into the air-vent 5. As a result, no air is trapped in the through-hole 3 or air-vent 5, and unhardened synthetic resin fills the interior of those conduits without voids.

For the artificial teeth 2 in FIGS. 6 and 7, step 4 processing causes unhardened synthetic resin in viscous fluid form to flow from the slit 6 and through-hole 3 established in each artificial tooth 3 into the air-vent 5 to increase the strength of connection between the denture base 4 and the artificial teeth 2. Unhardened synthetic resin filling the plaster mold chamber flows into the interior of each through-hole 3 from the openings at both ends of the through-hole 3 and from the slit 6. Unhardened synthetic resin flowing into the through-hole 3 flows from the through-hole 3 into the air-vent 5. At that time, air residing in the through-hole 3 and slit 6 is discharged from the air-vent 5 opening.

Finally, for the artificial teeth 2 in FIGS. 8 and 9, step 4 processing causes unhardened synthetic resin in viscous fluid form to flow from the vertical hole 7 and through-hole 3 established in each artificial tooth 3 into the air-vent 5 to increase the strength of connection between the denture base 4 and the artificial teeth 2. Unhardened synthetic resin filling the plaster mold chamber flows into the interior of each through-hole 3 from the openings at both ends of the through-hole 3 and from the vertical hole 7. Unhardened synthetic resin flowing into the through-hole 3 flows from the through-hole 3 into the air-vent 5. At that time, air residing in the vertical hole 7 and the through-hole 3 is discharged from the air-vent 5 opening.

As described above, when unhardened synthetic resin flows into the through-hole 3, air inside the through-hole 3 and air-vent 5 is discharged from the air-vent 5 opening and no air is trapped inside the through-hole 3 or air-vent 5. Accordingly, unhardened resin fills the through-hole 3 and air-vent 5 without creating voids. Further, as the same type of acrylic resin materials with similar chemical properties, the artificial teeth 2 and the denture base 4 can be solidly connected together. In this type of denture 1, denture base 4 acrylic resin is polymerized and hardened, resin in the through-hole 3 and air-vent 5 inside each artificial tooth 2 forms as a single unit with the denture base 4 resin, and adhesion between the resin and each artificial tooth 2 is increased by use of similar materials. Consequently, artificial teeth 3 can be robustly connected with the denture base 4 to yield a highly stable denture 1.

The invention claimed is:

1. A denture comprising:
   a denture base formed from plastic; and
   an artificial tooth with a root that is embedded in the denture base,
   wherein the artificial tooth is provided with a through-hole in the root that is filled with denture base plastic, and openings at respective opposite ends of the through-hole are embedded in the denture base,
   wherein each of the opposite ends of the through-hole established in the artificial tooth opens on a surface that faces an adjacent tooth,
   wherein an air-vent is defined in the artificial tooth so as to communicate with the through-hole inside the artificial tooth,
   wherein an opening for the air-vent is positioned on a lingual side surface of the artificial tooth that is exposed from the denture base,
   wherein denture base plastic is injected into the through-hole such that the denture base plastic flows into the air-vent from the through-hole so as to embed the root of the artificial tooth in the denture base,
   wherein an elongated slit is defined in the root of the artificial tooth, a first end of the slit communicates with the through-hole, a second end of the slit opens on a rear side of the root of the artificial tooth that is embedded in the denture base, and the denture base plastic is injected into the slit,
   wherein the air-vent is substantially perpendicular to the elongated slit, and wherein the slit intersects with the through-hole to form a cut-out region that is within a diameter of the through-hole.

2. The denture as cited in claim 1, wherein the through-hole and air-vent have circular cylindrical shapes with equal inside diameters.

3. The denture as cited in claim 1, wherein an interior width of the slit is smaller than an inside diameter of the through-hole.

4. The denture as cited in claim 1, wherein the slit extends in a direction of a row of teeth and each of opposite ends of the slit opens on a surface facing an adjacent tooth.

5. The denture as cited in claim 1, wherein a width of the slit and a width of the root are coextensive.

6. An artificial tooth including:
   a root embedded in a plastic denture base, and a through-hole established in the root, wherein denture base plastic is injected into the through-hole so as to fill the through-hole and attach and embed the artificial tooth in the denture base, wherein each of opposite ends of the through-hole established in the root opens on a surface that faces an adjacent tooth, wherein an air-vent is defined in the artificial tooth so as to communicate with the through-hole inside the artificial tooth, wherein an opening for the air-vent is positioned on a lingual side surface of the artificial tooth that is exposed from the denture base, wherein the denture base plastic is configured to flow into the air-vent from the through-hole, wherein an elongated slit is defined in the root of the artificial tooth, a first end of the slit communicates with the through-hole, a second end of the slit opens on a rear side of the root of the artificial tooth that is embedded in the denture base, and the denture base plastic is injected into the slit, wherein the air-vent is substantially perpendicular to the elongated slit, and wherein the slit intersects with the through-hole to form a cut-out region that is within a diameter of the through-hole.

7. The artificial tooth as cited in claim 6, wherein the through-hole and air-vent have circular cylindrical shapes with equal inside diameters.

8. The artificial tooth as cited in claim 6, wherein an interior width of the slit is smaller than an inside diameter of the through-hole.

9. The artificial tooth as cited in claim 6, wherein the slit extends in a direction of a row of teeth and each of opposite ends of the slit opens on a surface facing an adjacent tooth.

10. The artificial tooth as cited in claim 6, wherein a width of the slit and a width of the root are coextensive.

11. A method of attaching an artificial tooth to a denture base comprising:

establishing a through-hole in a root of the artificial tooth that is designed to be filled with denture base plastic, and has openings at respective opposite ends of the through-hole in respective surfaces that face respective adjacent teeth;

establishing an air-vent that is defined to communicate with the through-hole inside the artificial tooth, and has an opening positioned on a lingual side surface of the artificial tooth that is exposed from the denture base;

injecting denture base plastic into the through-hole such that the denture base plastic flows into the air-vent from the through-hole and embedding and attaching the root of the artificial tooth in the denture base such that the openings at the respective opposite ends of the through-hole are embedded in the denture base; and defining an elongated slit in the root of the artificial tooth, a first end of the slit communicating with the through-hole, a second end of the slit opening on a rear side of the root of the artificial tooth that is embedded in the denture base, the denture base plastic being injected into the slit, and the slit intersecting with the through-hole to form a cut-out region that is within a diameter of the through-hole.

12. The method of attaching the artificial tooth to the denture base as cited in claim 11, wherein an elongated slit is defined in the root of the artificial tooth, a first end of the slit communicates with the through-hole, a second end of the slit opens on a rear side of the root of the artificial tooth that is embedded in the denture base, and the denture base plastic is injected into the slit, and wherein the air-vent is substantially perpendicular to the elongated slit.

13. The method of attaching the artificial tooth to the denture base as cited in claim 12, wherein a width of the slit and a width of the root are coextensive.

* * * * *